United States Patent [19]

Newsome et al.

[11] Patent Number: 4,596,818
[45] Date of Patent: Jun. 24, 1986

[54] AMIDINES

[75] Inventors: Peter M. Newsome, Cheam; Lee J. Beeley, Dorking; Stephen F. Moss, Carshalton; Geoffrey H. Baker, Wallington, all of England

[73] Assignee: Beecham Group p.l.c., United Kingdom

[21] Appl. No.: 580,691

[22] Filed: Feb. 16, 1984

[30] Foreign Application Priority Data

Feb. 18, 1983 [GB] United Kingdom ............... 8304593

[51] Int. Cl.⁴ .................. A61K 31/38; A61K 31/415; C07D 233/22; C07D 233/44
[52] U.S. Cl. .................... 514/401; 514/402; 548/348; 548/351
[58] Field of Search ............... 548/351, 348; 424/273 R; 514/401, 402

[56] References Cited

U.S. PATENT DOCUMENTS

| 4,036,972 | 7/1977 | Stahle et al. | 548/348 X |
| 4,100,292 | 7/1978 | Stähle et al. | 548/351 X |
| 4,215,133 | 7/1980 | Stähle et al. | 548/348 X |
| 4,450,170 | 5/1984 | Beeley et al. | 548/351 X |

FOREIGN PATENT DOCUMENTS 0043659 1/1982 European Pat. Off. ............ 548/351

Primary Examiner—Joseph Paul Brust
Attorney, Agent, or Firm—Hopgood, Calimafde, Kalil, Blaustein & Judlowe

[57] ABSTRACT

A compound of formula (I):

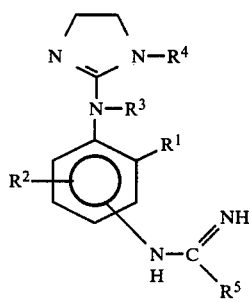

or a salt thereof wherein
$R^1$ is halogen, $C_{1-4}$ alkyl or $C_{1-4}$ alkoxy
$R^2$ is hydrogen, halogen, $C_{1-4}$ alkyl or $C_{1-4}$ alkoxy
$R^3$ and $R^4$ are the same or different and each is hydrogen, $C_{1-4}$ alkyl or acyl and
$R^5$ is either (i)

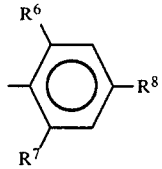

wherein
$R^6$, $R^7$ and $R^8$ are the same or different and each is selected from hydrogen, halogen, alkyl, alkoxy, hydroxy, hydroxyalkyl, alkoxyalkyl, mercapto, mercaptoalkyl, amino, aminoalkyl, nitro, cyano, carboxy or a salt, ester or amide of carboxy provided that at least one of $R^6$, $R^7$ and $R^8$ is other than hydrogen or (ii)

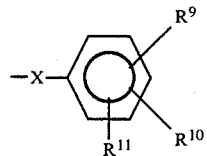

wherein
$R^9$, $R^{10}$ and $R^{11}$ are the same or different and each is selected from hydrogen, halogen, alkyl, alkoxy, hydroxy, hydroxyalkyl, alkoxyalkyl, mercapto, mercaptoalkyl, amino, aminoalkyl, nitro, cyano, carboxy or a salt, ester or amide of carboxy
and X is —CH₂— or —CH=CH— or (iii)

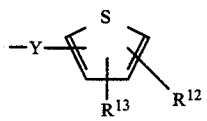

wherein
$R^{12}$ and $R^{13}$ are the same or different and each is selected from hydrogen, halogen, alkyl, alkoxy, hydroxy, hydroxyalkyl, alkoxyalkyl, mercapto, mercaptoalkyl, amino, aminoalkyl, nitro, cyano, carboxy or a salt, ester or amide of carboxy
and Y is a bond or —CH₂—.

7 Claims, No Drawings

AMIDINES

The present invention relates to certain amidinophenyliminoimidazolidines and to their use in treating diarrhoea and scours.

European Patent Application No. 0 043 659 discloses a class of phenyliminoimidazolidines having a nitrogen-containing substituent on the phenyl group. It has now been discovered that certain amidino derivatives falling within the broadest disclosure but not specifically mentioned in that application, have significant advantages in protecting young animals from death due to scours.

Accordingly the present invention provides a compound of formula (I):

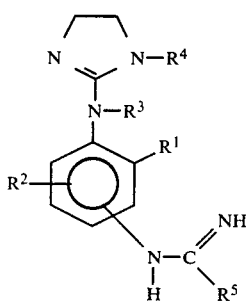

or a salt thereof wherein
$R^1$ is halogen, $C_{1-4}$ alkyl or $C_{1-4}$ alkoxy
$R^2$ is hydrogen, halogen, $C_{1-4}$ alkyl or $C_{1-4}$ alkoxy
$R^3$ and $R^4$ are the same or different and each is hydrogen, $C_{1-4}$ alkyl or acyl and
$R^5$ is either (i)

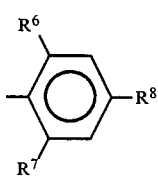

wherein
$R^6$, $R^7$ and $R^8$ are the same or different and each is selected from hydrogen, halogen, alkyl, alkoxy, hydroxy, hydroxyalkyl, alkoxyalkyl, mercapto, mercaptoalkyl, amino, aminoalkyl, nitro, cyano, carboxy or a salt, ester or amide of carboxy provided that at least one of $R^6$, $R^7$ and $R^8$ is other than hydrogen or (ii)

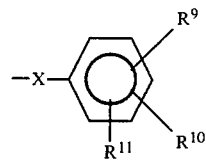

wherein
$R^9$, $R^{10}$ and $R^{11}$ are the same or different and each is selected from hydrogen, halogen, alkyl, alkoxy, hydroxy, hydroxyalkyl, alkoxyalkyl, mercapto, mercaptoalkyl, amino, aminoalkyl, nitro, cyano, carboxy or a salt, ester or amide of carboxy
and X is —CH$_2$— or —CH=CH— or (iii)

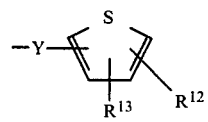

wherein
$R^{12}$ and $R^{13}$ are the same or different and each is selected from hydrogen, halogen, alkyl, alkoxy, hydroxy, hydroxyalkyl, alkoxyalkyl, mercapto, mercaptoalkyl, amino, aminoalkyl, nitro, cyano, carboxy or a salt, ester or amide of carboxy
and Y is a bond or —CH$_2$—.

It will be appreciated that compound of formula (I) may exist in several tautomeric forms, such as

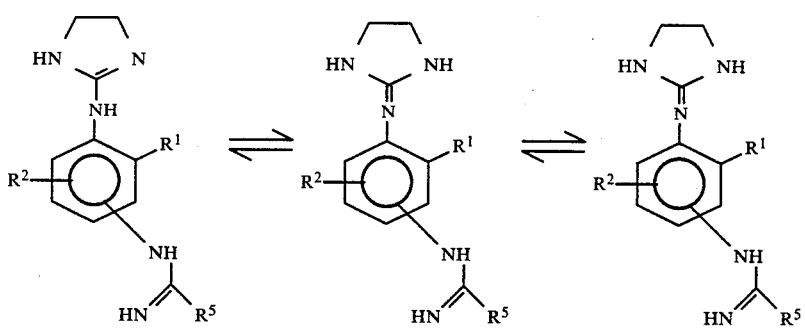

All these are encompassed by the invention.

Suitable salts of the compounds of formula (I) are acid addition salts, especially acid addition salts of pharmaceutically acceptable acids such as hydrochloric, hydroiodic, hydrobromic, nitric, sulphuric, citric, tartaric and pamoic acids.

Suitable N-acyl derivatives are those wherein the acyl group is the residue of an alkanoic acid.

Suitable salts of carboxy are alkali metal, alkaline earth metal and ammonium salts, especially sodium, potassium, magnesium, calcium and ammonium salts.

Suitable esters of carboxy are alkyl, phenyl and benzyl esters.

Suitable amides of carboxy are the unsubstituted amide and mono- or di-alkylamides.

Suitably the alkyl and alkoxy radicals mentioned above have from 1 to 4 carbon atoms; preferred alkyl groups are methyl and ethyl and preferred alkoxy groups are methoxy and ethoxy.

When $R^5$ is a group

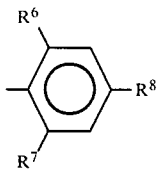

it is preferred that
(i) $R^8$ is halogen or methyl and $R^6$ and $R^7$ are both hydrogen or
(ii) $R^8$ is hydrogen and $R^6$ and $R^7$ are both halogen, both hydrogen, or one is halogen and the other is hydrogen.

When $R^5$ is a group

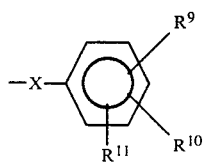

it is preferred that $R^9$, $R^{10}$ and $R^{11}$ are all hydrogen, or that two of $R^9$, $R^{10}$ and $R^{11}$ are hydrogen and the third is halogen, preferably in the para position.

When $R^5$ is a group

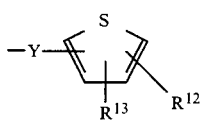

it is preferred that both $R^{12}$ and $R^{13}$ are hydrogen.

A preferred class of compounds within formula (I) are those of formula (IA)

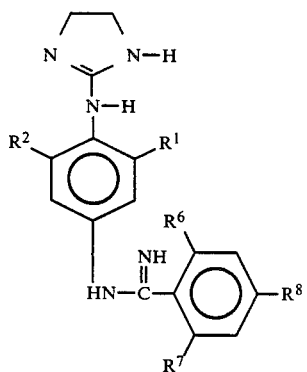

(IA)

wherein $R^1$, $R^2$, $R^6$, $R^7$ and $R^8$ are as defined in relation to compounds of formula (I).

Preferred compounds of formula (IA) are those wherein $R_1$ is hydrogen, chloro or methyl.

Preferred compounds of formula (IA) are those wherein $R_1$ and $R^2$ are the same.

Preferred compounds of formula (IA) are those wherein $R^1$ and $R^2$ are both methyl or, preferably both chloro.

Preferred compounds of formula (IA) are those wherein $R^6$ and $R^7$ are hydrogen and $R^8$ is halogen or $C_{1-4}$ alkyl.

A second class of preferred compounds within formula (I) are those of formula (IB).

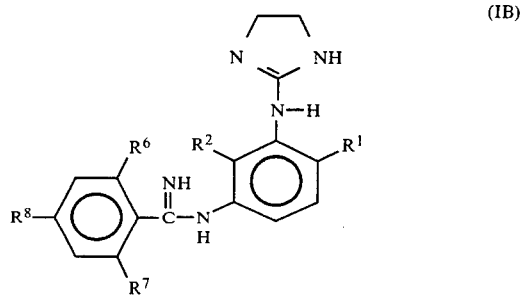

wherein
$R^1$, $R^6$, $R^7$ and $R^8$ are as defined in relation to compounds of formula (I) and
$R^2$ is hydrogen.

Preferred compounds of formula (IB) are those wherein $R^6$ and $R^7$ are hydrogen and $R^8$ is halogen.

Particularly preferred compounds of formula (I) are the following:
2-[4-(4-Chlorobenzamidino)-2,6-dichlorophenylimino]imidazolidine
2-[4-(4-Methylbenzamidino)-2,6-dichlorophenylimino]imidazolidine
2-[2,6-Dichloro-4-(4-fluorobenzamidino)-phenylimino]imidazolidine
2-[4-(4-Bromobenzamidino)-2,6-dichlorophenylimino]imidazolidine
2-[4-(4-Chlorobenzamidino)-2,6-dimethylphenylimino]imidazolidine
2-[4-(2-Fluorobenzamidino)-2,6-dichlorophenylimino]imidazolidine
2-[4-(2,6-Dichlorobenzamidino)-2,6-dichlorophenylimino]imidazolidine
2-[4-(2-Thenamidino)-2,6-dichlorphenylimino]imidazolidine
2-[4-Cinnamidino-2,6-dichlorophenylimino]imidazolidine
2-[4-(4-Fluorobenzylamidino)-2,6-dichlorophenylimino]imidazolidine
2-[2-Chloro-5-(3-thiopheneacetamidino)-phenylimino]imidazolidine and
2-[2-Chloro-5-(4-fluorobenzamidino)-phenylimino]imidazolidine and acid addition salts thereof.

The present invention also provides a process for producing compounds of formula (I) which process comprises either
(a) reacting a compound of formula (II):

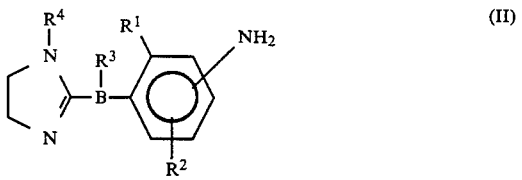

wherein $R^1$, $R^2$, $R^3$ and $R^4$ are as defined in relation to formula (I) with a compound of formula (III):

$R^5$—CN          (III)

wherein $R^5$ is as defined in relation to formula (I) or
(b) reacting a compound of formula (IV):

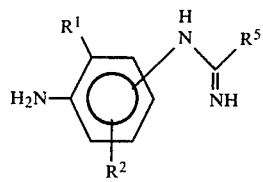

wherein $R^1$, $R^2$ and $R^5$ are as defined in relation to formula (I) with a compound of formula (V):

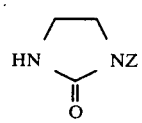

wherein Z is a protecting group, preferably acetyl, and, if necessary, thereafter removing the protecting group and optionally thereafter converting the compound of formula (I) into a further compound of formula (I) and/or into a salt thereof.

The reaction between compounds of formulae (II) and (III) may be achieved using conventional reagents and conditions, such as aluminium trichloride at high temperature. Compounds of formula (II) are disclosed in European Patent Application No. 0 070 084 and compounds of formula (III) are readily available commercially or can be made by conventional methods.

The reaction between compounds of formulae (IV) and (V) may be achieved using conventional conditions such as treating the compounds with phosphorus oxychloride in an inert solvent. The protecting group may be removed by conventional methods such as acid or base hydrolysis. Compounds of formula (IV) can be produced by methods analogous to those for producing compounds of formula (I) from compounds of formulae (II) and (III) as described above. Starting materials and compounds of formula (V) are readily available or may be produced by conventional methods.

Compounds of formula (I) protect animals from death due to scours caused by enteropathogenic E. coli and are therefore useful in the treatment of neonatal scours, especially in farm animals such as cattle and pigs, and in diarrhoea especially in humans.

The present invention therefore provides a compound of formula (I) for use in human or veterinary medicine.

The present invention further provides pharmaceutical or veterinary composition comprising a compound of formula (I) (hereinafter referred to as the 'drug') and a pharmaceutically or veterinarily acceptable carrier therefor.

Pharmaceutical and veterinary compositions of the drug will, of course, be adapted for administration to the humans or animals to be treated. Thus, for example, the composition may be a shaped composition, such as a bolus, tablet or capsule. In such cases the pharmaceutically or veterinarily acceptable carrier will be chosen from the usual range of lubricants, dispersants, binders, fillers and the like. When these shaped compositions are for administration to cattle and pigs often they will weigh at least 1 g, on occasions at least 2 g.

For administration to humans, especially children, the drug may suitably be presented as a syrup including suitable colouring and/or flavoring agents. Such syrups are conveniently presented in unit or multi-dose containers.

For veterinary use the composition may also be a dispersion or a solution of the drug in a suitable vehicle for use with an oral doser (this is a well known item of farm equipment, bascially comprising a liquid reservoir, a mouthpiece adapted for insertion into animals mouths, and a pump mechanism whereby unit doses can be ejected from the reservoir through the mouthpiece). Conveniently the drug may be administered from an oral doser as an aqueous solution. Alternatively, the vehicle will be an oil or water based cream to ensure homogeneity of the unit doses administered.

The invention, therefore, also provides an oral doser containing a multi-dose of the drug in a veterinarily acceptable vehicle.

The drugs of the invention may also be added to the animal feed or drinking water. Thus the invention also provides animal feed or animal drinking water containing a compound of formula (I). It will be convenient to formulate these animal feed and drinking water compositions with a multi-dose of the drug so that the animal takes in an appropriate quantity of the drug along with its diet. It will also be convenient to present the composition of the invention as a pre-mix for addition to the feed or drinking water.

With human babies or young animals, a particularly useful technique is to blend their milk with the drugs of this invention.

The compositions of the invention may also be formulated for injection. In such cases the drug chosen is suitably dissolved in water for injection.

Often it will be appropriate to include in the compositions a further medicine such as an antibacterial agent for example an antibiotic such as amoxycillin or neomycin or a sulphonamide such as sulfadoxin.

Treatment of diarrhoea and scours using the drug may be supplemented by oral rehydration therapy such as those described in U.K. Pat. No. 1,581,826 and German Offenlegungsschrift No. 28 54 281, UK Patent Application No. 2 012 163A, U.S. Pat. No. 3 898 328, Nalin, D. R. and Cash, R. A., Bull. World Health Org., 43, 361 (1970), French Pat. No. 2 467 599, UK Patent No. 1 465 308 and as described in 'Secretory Diarrhoea', Ed M. Field, J. S. Fordtran and S, G, Schultz, American Physiological Society, Maryland, 1980 pp 179–185 and Lancet, (1975) pp 79 and 80. Conveniently the drug may be administered with the oral rehydration formulation. Alternatively it may be provided separately and administered simultaneously or sequentially with the oral rehydration formulation.

The amount of drug administered must, of course, be sufficient to bring about the desired effect and will also depend on the body weight of the recipient and the chosen route of administration. Thus, by way of example, useful dosage units of the composition for treating diarrhoea may contain 1 µg to 200 mg of the drug, more suitably 100 µg to 100 mg. Of course, it will be appreciated that many preferred compositions of the invention are in multi-dose form as, for the therapy of animals, it is often most desirable to be able rapidly to treat a number of animals. Such multi-dose compositions will contain, by way of example, at least 1 mg of the drug. Depending on the exact nature of the said multi-dose composition, often it will contain at least 50 mg of the drug, and on occasions as much as 1 g. Doses may be administered once or several times daily.

The present invention further provides a method for treating humans and animals for diarrhoea, which method comprises administering an effective, non-toxic amount of a compound of formula (I) to the sufferer.

In a particular aspect the method of treatment comprises the administration of a pharmaceutical or veterinary composition of a compound of formula (I), as hereinbefore described.

The present invention will now be illustrated by the following Examples which are not intended to limit the invention in any way.

PREPARATION OF BENZAMIDINES—GENERAL METHOD FOR EXAMPLES 1 TO 12

The aminophenyliminoimidazolidine monohydrochloride (1 mol), and aluminium chloride (2 mol) were heated together with stirring at 130° C.–150° C. for ¾ hour and then the temperature was increased for 200° C. for 2½ hours. The mixture was cooled slightly and then added to water. This aqueous mixture was washed with methylene chloride and then basified, the resulting solid was filtered off. The solid was then extracted with methanol, filtered and evaporated. The residue was converted to the dihydrochloride in methanol with ethanolic hydrogen chloride and then recrystallised from acetone/methanol.

EXAMPLE 1

2-[4-(4-Chlorobenzamidino)-2,6-dichlorophenylimino]imidazolidine dihydrochloride 2-(4-Amino-2,6-dichlorophenylimino)imidazolidine, mono hydrochloride was treated with 4-chlorobenzonitrile and aluminium chloride as described. The title benzamidine dihydrochloride was isolated, mpt 215°–218° C.

Mass spectrum observed m/e=381.0320 (M+).
Calculated for $C_{16}H_{14}N_5Cl_3$=381.0314.

EXAMPLE 2

2-[4-(4-Methylbenzamidino)-2,6-dichlorophenylimino]imidazolidine dihydrochloride 2-(4-Amino-2,6-dichlorophenylimino)imidazolidine, monohydrochloride was treated with 4-tolunitrile and aluminium chloride as described. The title benzamidine dihydrochloride was isolated, mpt 271°–273° C.

Mass spectrum observed m/e=361.0057 (M+).
Calculated for $C_{17}H_{17}N_5Cl_2$=361.0059.

EXAMPLE 3

2-[2,6-Dichloro-4-(4-fluorobenzamidino)-phenylimino]imidazolidine dihydrochloride 2-(4-Amino-2,6-dichlorophenylimino)imidazolidine, monohydrochloride was treated with 4-fluorobenzonitrile and aluminium chloride as described. The title benzamidine dihydrochloride was isolated, mpt 275°–279° C.

Mass spectrum observed m/e=365.0617 (M+).
Calculated for $C_{16}H_{14}N_5Cl_2F$=365.0608.

EXAMPLE 4

2-[4-(4-Bromobenzamidino)-2,6-dichlorophenylimino]imidazolidine dihydrochloride 2-(4-Amino-2,6-dichlorophenylimino)imidazolidine, monohydrochloride was treated with 4-bromobenzonitrile and aluminium chloride as described. The title benzamidine dihydrochloride was isolated, mpt 258°–260° C.

Mass spectrum observed m/e=424.9832 (M+).
Calculated for $C_{16}H_{14}N_5BrCl_2$=424.9807.

EXAMPLE 5

2-[4-(4-Chlorobenzamidino)-2,6-dimethylphenylimino]imidazolidine dihydrochloride 2-(4-Amino-2,6-dimethylphenylimino)imidazolidine, monohydrochloride was treated with 4-chlorobenzonitrile and aluminium chloride as described. The title benzamidine dihydrochloride was isolated mpt 284°–286° C.

Mass spectrum observed m/e=341.1394 (M+).
Calculated for $C_{18}H_{20}N_5Cl$=341.1406.

EXAMPLE 6

2-[4-(2-Fluorobenzamidino)-2,6-dichlorophenylimino]imidazolidine dihydrochloride 2-(4-Amino-2,6-dichlorophenylimino)imidazolidine monohydrochloride was treated with 2-fluorobenzonitrile and aluminium chloride as described. The title benzamidine was isolated.

Mass spectrum observed m/e=365.0607 (M+).
Calculated for $C_{16}H_{14}N_5Cl_2F$=365.0609.

EXAMPLE 7

2-[4-(2,6-Dichlorobenzamidino)-2,6-dichlorophenylimino]imidazolidine dihydrochloride 2-(4-Amino-2,6-dichlorophenylimino)imidazolidine monohydrochloride was treated with 2,6-dichlorobenzonitrile and aluminium chloride as described. The title benzamidine was isolated.

Mass spectrum observed m/e=414.9920 (M+).
Calculated for $C_{16}H_{13}N_5Cl_4$=414.9923.

EXAMPLE 8

2-[4-(2-Thenamidino)-2,6-dichlorophenylimino]imidazolidine dihydrochloride 2-(4-Amino-2,6-dichlorophenylimino)imidazolidine monohydrochloride was treated with 2-thiophenecarbonitrile and aluminium chloride as described. The title benzamidine was isolated.

Mass spectrum m/e=353.0265 (M+).
Calculated for $C_{14}H_{13}N_5SCl_2$=353.0268.

EXAMPLE 9

2-[4-Cinnamidino-2,6-dichlorophenylimino]imidazolidine dihydrochloride 2-(4-Amino-2,6-dichlorophenylimino)imidazolidine monohydrochloride was treated with cinnamonitrile and aluminium chloride as described. The title benzamidine was isolated, m.p. 286°–88° C.

Analysis calculated for $C_{18}H_{20}Cl_4N_5$:
Theory=C48.34; H, 4.29; N, 15.65%.
Found=C47.79; H, 4.35; N, 15.15%.

EXAMPLE 10

2-[4-(4-Fluorobenzylamidino)-2,6-dichlorophenylimino]imidazolidine dihydrochloride 2-(4-Amino-2,6-dichlorophenylimino)imidazolidine monohydrochloride was treated with 4-fluorophenylacetonitrile and aluminium chloride as described. The title benzamidine was isolated, m.p. 190° C.

Mass spectrum observed m/e=379.0765 (M+).
Calculated for $C_{17}H_{16}N_5Cl_2F = 379.0766$.

EXAMPLE 11

2-[2-Chloro-5-(3-thiopheneacetamidino)-phenylimino]imidazolidine

2-[5-Amino-2-chlorophenylimino]imidazolidine monohydrochloride was treated with 3-thiopheneacetonitrile and aluminium chloride as described. After converting the benzamidine hydrochloride to the free base, the product was recrystallized from adcetonitrile to yield the title compound as white powder.

Mass spectrum observed m/e=333.0813 (M+).
Calculated for $C_{15}H_{16}N_5SCl = 333.0815$.

EXAMPLE 12

2-[2-Chloro-5-(4-fluorobenzamidino)-phenylimino]imidazolidine dihydrochloride

2-[5-Amino-2-chlorophenylimino]imidazolidine monohydrochloride was treated with 4-fluorobenzonitrile and aluminium chloride as described. A hydrate of the title benzamidine was isolated, m.p. 290° C.

Analysis calculated for $C_{16}H_{17}N_5Cl_3F \cdot 1.5H_2O$:
Theory=C, 44.5; H, 4.67; N, 16.21%.
Found=C, 44.61; H, 4.21; N, 16.37%.

BIOLOGICAL EVALUATION (i) Protection of Neonatal Mice from Lethal Enteropathogenic *E coli* Infection 4 day old mice were orally dosed with 50 μl of phosphate buffered saline containing $1 \times 10^5$ organisms/ml of *E coli* B44 (09:K90:K99) an enteropathogenic strain originaly isolated from a scouring calf. The mice were then dosed b.i.d. with either placebo or drug for four days commencing 16 hours after infection. The animals were left with their mothers throughout the experiment and a daily record of deaths was made. The experiment was terminated 10 days after infection. The mortality in the drug treated group was then compared with the mortality in the placebo group using the following formula:

% Reduction in mortality = $[(Mp-Md)/Mp] \times 100$ where
Mp=mortality in group receiving placebo
Md=mortality in group receiving drug
Statistical analysis was performed using $2 \times 2$ contingency tables (single tailed 'p'). Results are given in Table 1 in which 'Protection (%)' is the same as '% Reduction in mortality' above.

TABLE 1

| Ex | R¹ | R² | R⁵ | Dose (mg/kg) | Protection (%) | No of mice |
|---|---|---|---|---|---|---|
| 1 | Cl | Cl | 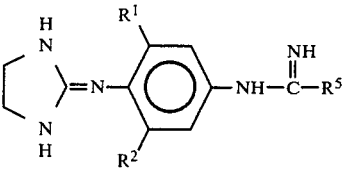 | 10<br>2<br>0.4 | 2<br>31(P < 0.01)<br>9 | 45<br>108<br>41 |
| 2 | Cl | Cl |  | 2<br>0.4<br>0.8 | 33(P < 0.05)<br>24<br>13 | 47<br>71<br>51 |
| 3 | Cl | Cl |  | 10<br>2<br>0.4 | 13<br>64(P < 0.001)<br>23 | 51<br>50<br>51 |
| 4 | Cl | Cl |  | 2<br>0.4 | 16<br>8 | 75<br>22 |
| 5 | Me | Me |  | 10 | 30 | 24 |
| 6 | Cl | Cl |  | 2 | 4 | 69 |
| 7 | Cl | Cl |  | 10 | 7 | 21 |
| 8 | Cl | Cl |  | 0.4 | 6 | 24 |
| 9 | Cl | Cl |  | 10 | 12 | 78 |
| 10 | Cl | Cl |  | 10 | 11 | 28 |
| 11 | Cl | H |  | 50<br>10<br>2 | 0<br>44(P < 0.05)<br>−5 | 20<br>42<br>20 |
| 12 | Cl | H |  | 10<br>2<br>0.4<br>0.8 | 33<br>35(P < 0.05)<br>26<br>5 | 41<br>46<br>42<br>60 |

We claim:

1. A compound of formula (I):

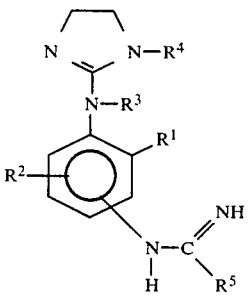

or an acid addition salt thereof wherein
R$^1$ is halogen, C$_{1-4}$ alkyl or C$_{1-4}$ alkoxy
R$^2$ is hydrogen, halogen, C$_{1-4}$ alkyl or C$_{1-4}$ alkoxy
R$^3$ and R$^4$ are the same or different and each is hydrogen, C$_{1-4}$ alkyl or acyl wherein the acyl group is the residue of an alkanoic acid and
R$^5$ is either (i)

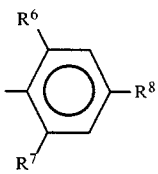

wherein R$^6$, R$^7$ and R$^8$ are the same or different and each is selected from hydrogen, halogen, alkyl, alkoxy, hydroxy, hydroxyalkyl, alkoxyalkyl, mercapto, mercaptoalkyl, —NH$_2$, aminoalkyl, nitro, cyano, carboxy or an alkali metal, alkaline earth metal, or ammonium salt, alkyl, phenyl, or benzyl ester or unsubstituted amides and mono—or di-alkylamides of carboxy provided that at least one of R$^6$, R$^7$ and R$^8$ is other than hydrogen or (ii)

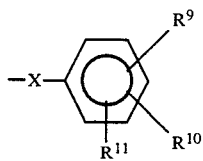

wherein
R$^9$, R$^{10}$ and R$^{11}$ are the same or different and each is selected from hydrogen, halogen, alkyl, alkoxy, hydroxy, hydroxyalkyl, alkoxyalkyl, mercapto, mercaptoalkyl, —NH$_2$, aminoalkyl, nitro, cyano, carboxy or an alkali metal, alkaline earth metal, or ammonium salt, alkyl, phenyl, or benzyl ester or unsubstituted amides and mono—or di—alkylamides of carboxy
and X is —CH$_2$—or—CH=CH—or (iii)

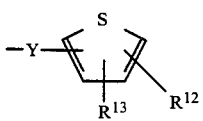

wherein
R$^{12}$ and R$^{13}$ are the same or different and each is selected from hydrogen, halogen, alkyl, alkoxy, hydroxy, hydroxyalkyl, alkoxyalkyl, mercapto, mercaptoalkyl, —NH$_2$, aminoalkyl, nitro, cyano, carboxy or an alkali metal, alkaline earth metal, or ammonium salt, alkyl, phenyl, or benzyl ester or unsubstituted amides and mono—or di-alkylamides of carboxy
and Y is a bond or—CH$_2$—.

2. A compound according to claim 1 and having formula (IA)

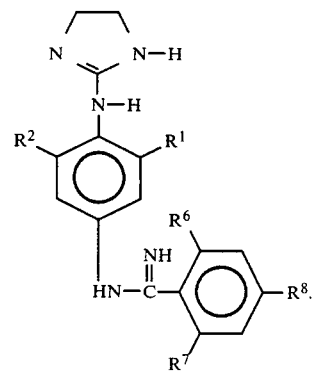

3. A compound according to claim 1 and having formula (1B)

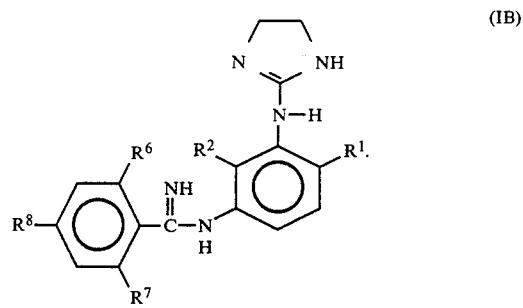

4. A compound according to claim 1 and selected from
2-[4-(4-Chlorobenzamidino)-2,6-dichlorophenylimino]imidazolidine
2-[4-(4-Methylbenzamidino)-2,6-dichlorophenylimino]imidazolidine
2-[2,6-Dichloro-4-(4-fluorobenzamidino)-phenylimino]imidazolidine
2-[4-(4-Bromobenzamidino)-2,6-dichlorophenylimino]imidazolidine
2-[4-(4-Chlorobenzamidino)-2,6-dimethylphenylimino]imidazolidine
2-[4-(2-Fluorobenzamidino)-2,6-dichlorophenylimino]imidazolidine
2-[4-(2,6-Dichlorobenzamidino)-2,6-dichlorophenylimino]imidazolidine
2-[4-(2-Thenamidino)-2,6-dichlorophenylimino]imidazolidine
2-[4-Cinnamidino-2,6-dichlorophenylimino]imidazolidine
2-[4-(4-Fluorobenzylamidino)-2,6-dichlorophenylimino]imidazolidine
2-[2-Chloro-5-(3-thiopheneacetamidino)-phenylimino]imidazolidine and 2-[2-Chloro-5-(4-fluorobenzamidino)-phenylimino]imidazolidine and acid addition salts thereof.

5. A pharmaceutical or veterinary composition comprising an anti-diarrhoeal or anti-scour effective amount of a compound of formula (I) as defined in claim 1 and a pharmaceutically or veterinarily acceptable carrier therefor.

6. A composition as claimed in claim 5 in unit dosage form.

7. A method for treating diarrhoea or scours in human and non-human animals comprising administering an anti-diarrhoeal or anti-scour effective, non-toxic amount of a compound as defined in claim 1 to a human or non-human animal in need thereof.

* * * * *